US007820382B2

(12) United States Patent
Bauer

(10) Patent No.: US 7,820,382 B2
(45) Date of Patent: Oct. 26, 2010

(54) METHOD FOR THE EARLY DETECTION OF BREAST CANCER, LUNG CANCER, PANCREATIC CANCER AND COLON POLYPS, GROWTHS AND CANCERS AS WELL AS OTHER GASTROINTESTINAL DISEASE CONDITIONS AND THE PREOPERATIVE AND POSTOPERATIVE MONITORING OF TRANSPLANTED ORGANS FROM THE DONOR AND IN THE RECIPIENT AND THEIR ASSOCIATED CONDITIONS RELATED AND UNRELATED TO THE ORGAN TRANSPLANTATION

(76) Inventor: A. Robert Bauer, P.O. Box 17533, Salt Lake City, UT (US) 84117-0533

( * ) Notice: Subject to any disclaimer, the term of this patent is extended or adjusted under 35 U.S.C. 154(b) by 1034 days.

(21) Appl. No.: 11/266,901

(22) Filed: Nov. 5, 2005

(65) Prior Publication Data
US 2006/0088876 A1    Apr. 27, 2006

Related U.S. Application Data

(63) Continuation-in-part of application No. 10/938,696, filed on Sep. 11, 2004, now abandoned.

(60) Provisional application No. 60/664,842, filed on Mar. 25, 2005, provisional application No. 60/676,670, filed on Apr. 30, 2005, provisional application No. 60/706,499, filed on Aug. 7, 2005, provisional application No. 60/598,477, filed on Aug. 3, 2004, provisional application No. 60/607,088, filed on Sep. 5, 2004.

(51) Int. Cl.
C12Q 1/68 (2006.01)
(52) U.S. Cl. ............................................. 435/6; 435/7.1
(58) Field of Classification Search ........................ None
See application file for complete search history.

(56) References Cited

U.S. PATENT DOCUMENTS

| 6,905,827 | B2 | 6/2005 | Wohlgemuth et al. |
| 2001/0051344 | A1 | 12/2001 | Shalon et al. |
| 2004/0009147 | A1 | 1/2004 | Ebner et al. |
| 2004/0110221 | A1 | 6/2004 | Twine et al. |
| 2004/0146921 | A1 | 7/2004 | Eveleigh et al. |
| 2004/0229349 | A1 | 11/2004 | Daridon |
| 2005/0152908 | A1 | 7/2005 | Liew et al. |
| 2007/0037144 | A1* | 2/2007 | Wohlgemuth et al. .......... 435/6 |

FOREIGN PATENT DOCUMENTS

| WO | WO 0020013 | 4/2000 |
| WO | WO 02/059367 A2 | 8/2002 |
| WO | WO-03-090694 A2 * | 11/2003 |
| WO | WO2004/048933 | 6/2004 |

OTHER PUBLICATIONS

Paweletz et al, in Microarrays and Cancer Research, 2002, Warrington et al (eds.), Eaton Publishing, Westborough, MA, pp. 61-77.*
Staynov et al, Immunology 75: 196 (1992).*
Villa-Komaroff et al, Methods Enzymol. 30: 709 (1974).*
Axis-Shield LymphoprepTM Product Description (Mar. 2003).*
Xu T, Shu CT, Purdom E, Dang D, Iisley D, Guo Y, Weber J, Holmes SP, Lee PP, Microarray analysis reveals differences in gene expressions of circulating CD8(+) T cells in melanoma patients and healthy donors, Cancer Research, May 15, 2004, 21(1), p. 21-4.
Hong, MH, Xiao XB, Mai HQ, Cao SM, Min HQ, Analysis of gene expression patterns of periphery lymphocytes in patients with nasopharyngeal carcinoma, Ai Zheng, Jan. 2002, 21(1), o. 21-4, www.ncbi.nlm.nih.gov/entrez/query.
Twine NC, Stover JA, Marshall B, Dukart G, Hidalgo M, Stadler W, Logan T, Dutcher J, Hudes G, Dorner AJ, Slonim DK, Trepicchio WL, Burczynski ME, Disease-associated expression profiles in peripheral blood mononuclear cells from patients with advanced renal cell carcinoma, Sep. 15, 2003, 6069-75, 63(18).
Thomas AM et al., Mesothelin-specific CD 8(+) T cell responses provide evidence of in vivo cross-priming by antigen-presenting cells in vaccinated pancreatic patients. J Exp Med., Aug. 2004, 200(3): 297-306.
McLaren PJ et al., Antigen-specific gene expression profiles of peripheral blood mononuclear cells do not reflect those T-lymphocyte subsets, Clin Diagn Lab Immunol, Sep. 2004, 11(5), 977-82.
Burczynski ME, Transcription profiles in peripheral blood mononuclear cells prognositic clinical outcomes in patients with advanced renal cell carcinoma, Clinical Cancer Research., Feb. 2005, 11(3), 1181-9.

(Continued)

*Primary Examiner*—James Martinell
(74) *Attorney, Agent, or Firm*—Thorpe North & Western LLP

(57) ABSTRACT

A method for the early diagnosis of breast, lung, pancreatic and colon growths and cancers as well as conditions associated with donor and recipient organ transplants, both before and after transplantation to identify and allow treatment of possible transplanted organ rejection and other disease conditions related and unrelated to the transplantation, compares the gene expression patterns from a patient's peripheral blood monocytes-lymphocyte's gene system with either the similar gene expression patterns of a normal person, or with the similar gene expression patterns of a person known to have the condition being screened for. Differences between the patient's gene expression patterns for particular genes and the normal patterns indicates the presence of the condition with the number of differences indicating the probability of the condition. Similarities between the patient's gene expression patterns for those particular genes and the patterns of a person known to have the condition indicates the presence of the condition with the number of similarities indicating the probability of the condition. For example, particular genes for use in identifying pancreatic cancer are disclosed.

17 Claims, 8 Drawing Sheets

OTHER PUBLICATIONS

Lucentini, J., Gene Association Studies Typically Wrong, The Scientist, 2004, 18(24):20.

Kroese et al. Genetic Tests and Their Evaluation: Can We Answer the Key Questions? Genetics in Medicie, 2004, 6(6): 475-480.

Deprimo, et al., Expression profiling of blood samples from an SU5416 Phase III metastatic colorectal cancer clinical trial: a novel strategy for biomarker identification, Feb. 7, 2003, 12 pages, 3:3, http://www.biomedcentral.com/1471-2407/3/3.

Lockhart et al., Expression Monitoring by Hybridization to High-Density Oligonucleotide Arrays, Nature Biotechnology, 1996, 1675-1680, (14)13.

Ringel et al., (Proceeding of the American Association of Cancer Research (2001) vol. 42 p. 616, abstract 3311).

Benner et al., (Trends in Genetics (2001) vol. 17, pp. 414-418).

Vandesompele et al., (Genome Biology(2002) vol. 3, pp. 1-11.

Cheung et al., (Nature Genetics, 2003, vol. 33, pp. 422-425).

Wu (Journal of Pathology, 2001, vol. 195, pp. 53-65).

Newton et al., (Journal of Computational Biology, 2001, vol. 8, pp. 37-52).

NCBI website. Nucleotide search-alcam-Nucleotide Results. (http://ncbi.nlm.nih.gov/sites/entrez) (pp. 1-2, Oct. 29, 2008).

Oncogenomics website. Pediatric Xenograft & Tumor Gene Expression Database—Details page (http://pob.abcc.ncifcrf.gov/cgi-bin/JK) Oct. 28, 2008, pp. 1-3.

Mannick et al., Gene expression in mononuclear cells from patients with inflammatory bowel disease. Clinical Immunology 112 (2004) 247-257.

GenBank accession NM_145345.1 GI:21703361 (Sep. 3, 2004).

Oncogenomics (download Sep. 30, 2009).

GenBank Accession NM_183008.2 GI:41281992 (Jan. 2004).

Entrez Gene 91544 (downloaded Sep. 30, 2009).

LaTulippe et al (Cancer Research (2002) vol. 62, pp. 4499).

Affymetrix (website Downloaded Mar. 13, 2010). Probe Sets HG-U95D:86652_AT, HG-U95AV2:41409_AT, HG-95E:67449_F_AT, and HG-U95B:58233_AT.

Greenbaum et at (Genome Biology 2003, vol. 4, article 117, pp. 1-8).

\* cited by examiner

METHOD FOR THE EARLY DETECTION OF BREAST CANCER, LUNG CANCER, PANCREATIC CANCER AND COLON POLYPS, GROWTHS AND CANCERS AS WELL AS OTHER GASTROINTESTINAL DISEASE CONDITIONS AND THE PREOPERATIVE AND POSTOPERATIVE MONITORING OF TRANSPLANTED ORGANS FROM THE DONOR AND IN THE RECIPIENT AND THEIR ASSOCIATED CONDITIONS RELATED AND UNRELATED TO THE ORGAN TRANSPLANTATION

RELATED APPLICATIONS

This is a continuation-in-part of copending application Ser. No. 10/938,696, filed Sep. 11, 2004 now abandoned, and entitled 'The Discovery and a Method for the Early Detection of Pancreatic Cancer and other Disease Conditions', and this application claims the benefit of Provisional Patent Application No. 60/598,477, filed Aug. 3, 2004, entitled "Process for Early Identification of Cancer and Other Disease Conditions," Provisional Application No. 60/607,088, filed Sep. 5, 2004, entitled "The Discovery and a Method for the Early Detection of Pancreatic Cancer and Other Disease Conditions", Provisional Patent Application No. 60/664,842, filed Mar. 25, 2005, entitled "A Method for the Early Detection of Pancreatic Cancer and Other Gastrointestinal Disease Conditions," Provisional Patent Application No. 60/676,670, filed Apr. 30, 2005, entitled "A Method For The Early Detection Of Pancreatic Cancer And Other Gastrointestinal Disease Conditions." Provisional Patent Application No. 60/706,499, filed Aug. 7, 2005, entitled "Method for the Early Detection of Pancreatic Cancer and Other Gastrointestinal Disease Conditions." Applicant also makes reference to Disclosure Document No. 532619, filed Jun. 5, 2003 (referred to in parent application Ser. No. 10/938,696), entitled "The Method For A Useful Process for the Early Identification Of Cancer," Disclosure Document No. 560475, filed Sep. 10, 2004 (referred to in parent application Ser. No. 10/938,696), entitled "The Discovery and a Method for the Early Detection of Pancreatic Cancer and Other Disease Conditions," Disclosure Documents No. 572656, filed Mar. 6, 2005, entitled "Gene Expression Diagnosis of Pancreatic Cancer (Intraductal Pancreatic Adenocarcinoma) and Other Gastrointestinal Growths and Conditions from Peripheral Blood Lymphocytes," Disclosure Documents No. 573431, filed Mar. 22, 2005, entitled "Gene Expression Diagnosis of Pancreatic Cancer (Intraductal Pancreatic Adenocarcinoma) and Other Gastrointestinal Growths and Conditions from Peripheral Blood Lymphocytes," and Disclosure Document No. 574718, filed Apr. 15, 2005, entitled "Gene Expression Diagnosis of Pancreatic Cancer (Intraductal Pancreatic Adenocarcinoma) and Other Gastrointestinal Growths and Conditions from Peripheral Blood Lymphocytes." All of the above applications and disclosure documents are hereby incorporated herein by reference.

BACKGROUND OF THE INVENTION

1. Field

This invention is in the field of methods for diagnosis and appraisal of treatment of disease conditions.

2. State of the Art

Breast cancer, lung cancer, colon cancers, pancreatic cancers and related pre-cancer growths are a very serious concern for the citizens of the United States and the world. The morbidity and mortality from these conditions is source of considerable physical and economic distress to the populations of this country and countries of the world. Jemal A et al. *Cancer Statistics* 2004, CA Cancer J Clin, 2005 54(1): 118-129. The treatment of growths, cancers and other disease conditions of organs often requires their replacement with a transplanted organ from another person or mammalian creature. The pre-transplantation evaluation of the donor and the recipient of the transplanted organ as well as the post transplant evaluation of the recipient for rejection of the transplant and the development of other diseases related and unrelated to the transplantation treatment is also a daunting task. There is clearly a need for better markers to indicate the state of disease and growing tumors, as well as the pre and post transplant clinical status of donor and recipient. If growths of the breast, lung, pancreas and colon are detected sooner with better markers the chances of successful cure are greatly improved.

Since the dividing time of the cells in most growths are several days, the growth usually has been present for many months or years before it is detectable by present imaging and other diagnostic methods. Pathway markers have not as yet proved successful in the early diagnosis of most of these growths with a high degree of specificity or sensitivity.

With the development of tumors, dendritic cells or macrophages note new growth, whether of genetic or epigenetic origin, by recognizing the altered proteins, often presented on the cancer cell's surface through their receptor channels. The dendritic cells convey these altered protein changes to the lymphocytes with the addition of major histocompatibility complexes. This includes T. lymphocytes CD8 with HCS I and CD4 with HCS II. The B lymphocytes are subsequently programmed by the recognizing T lymphocyte. Zeng, G., *MHC Class II-Restricted Tumor Antigens Recognized by CD4+ T Cells: New Strategies for Cancer Vaccine Design*. J Immunother, 2001. 24(3): p. 195-204; Jonuleit, H., et al., *Identification and functional characterization of human CD4 (+)CD25(+) T cells with regulatory properties isolated from peripheral blood*. J Exp Med, 2001. 193(11): p. 1285-94; Serbina N. V., Pamer E. G. *Giving Credit Where Credit Is Due*. Science, 2003, 301:1856-1857; and Baxevanis, C. N., et al., *Tumor-specific CD4+ T lymphocytes from cancer patients are required for optimal induction of cytotoxic T cells against the autologous tumor*. J Immunol, 2000. 164(7): p. 3902-12. Through this mechanism, the lymphocytes specifically recognize the new growth and program specifically against it, sending tumor infiltrating lymphocytes or TIL cells to the new growth. These TIL cells may decrease in the area of the tumor as tolerance for the tumor develops. Ryschich, E., et al., *Transformation of the microvascular system during multistage tumorigenesis*. Int J Cancer, 2002. 97(6): p. 719-25. It has been shown that the CD4-CD25 T lymphocytes contribute to tolerance of developing cancer. Liyanage, U. K., et al., *Prevalence of regulatory T cells is increased in peripheral blood and tumor microenvironment of patients with pancreas or breast adenocarcinoma*. J Immunol, 2002. 169(5): p. 2756-61. The use of peripheral blood lymphocytes for diagnosis of certain diseases have been proposed and described in Hong M H, X. X., Mai H Q, Cao S M Min H Q, *Analysis of gene expression patterns of periphery lymphocytes in patients with nasopharyngeal carcinoma*. Ai Zheng, 2002. 21(1): p. 21-4; Xu T et al *Microarray analysis reveals differences in gene expression of circulating CD8+ T cells in melanoma patients and healthy donors*. Cancer Res. 2004 May 15; 64(10):3661-7; Thomas A M et al. *Mesothelin-specific CD8 (+) T cell responses provide evidence of in vivo cross-priming by antigen-presenting cells in vaccinated pancreatic cancer patients*. J. Exp Med. 2004 Aug. 2; 200(3): 297-306; and McLaren P J et al *Antigen-specific gene expression profiles of peripheral blood mononuclear cells do not reflect those of T-lymphocyte subsets*. Clin Diagn Lab Immunol. 2004 September; 11(5):977-82. Twine & Burczynski. Twine N C, et al. *Disease-associated expression profiles in peripheral blood mononuclear cells from patients with advanced renal cell carcinoma*. Cancer Res. 2003 Sep. 15; 63(18):6069-75. Burczynski M E, Twine N C et. al. *Transcriptional profiles in peripheral blood mononuclear cells prognostic of clinical outcomes in patients with advanced renal cell carcinoma.* Clinical Cancer Res. 2005 Feb. 1; 11(3):1181-9.

SUMMARY OF THE INVENTION

As indicated above, dendritic cells in a body convey altered protein changes resulting from a change in a body's condition to the lymphocytes with the addition of major histocompatibility complexes. This includes T. lymphocytes CD8 with HCS I and CD4 with HCS II. The B lymphocytes are subsequently programmed by the recognizing T lymphocyte. Because of this, a body's peripheral blood monocyte-lymphocyte's gene system should recognize and continue to react to changes in a body's condition, such as a developing neoplasm. According to the invention, it has been found that this recognition and reaction to changes in a body's condition changes the body's peripheral blood monocyte-lymphocyte's gene system. The state of the body's peripheral blood monocyte-lymphocyte's gene system can be determined by determining the gene expression characteristics of genes of the body's peripheral blood monocyte-lymphocytes. By comparing the monocyte-lymphocyte gene expression characteristics of the monocyte-lymphocyte genes from a group of bodies having a certain known condition with the monocyte-lymphocyte gene expression characteristics of similar peripheral blood monocyte-lymphocytes from a group of bodies known not to have the certain condition, a number of specific genes likely to show different gene expressions between the group known to have the certain condition and the group known not to have the certain condition can be identified. While it may not be possible to pick out one or more particular genes which will always be expressed differently between a body with the certain condition and one without the certain condition, and errors can occur in the determination of individual gene expression characteristics, where the expression characteristics of a number of genes are found likely to be different between the monocyte-lymphocyte genes of a body with the certain condition and a body without the certain condition, an indication is given by a difference in the expression of one or more of the identified genes. The number of identified genes showing a different expression as well as the particular genes showing a different expression provides an indication of the degree of probability of the existence of the condition.

By comparing the monocyte-lymphocyte gene expression characteristics of the monocyte-lymphocyte genes from the group of bodies having the certain known condition with the monocyte-lymphocyte gene expression characteristics of similar peripheral blood monocyte-lymphocytes from the group of bodies known not to have the certain condition, a "normal differential gene expression pattern" typical of a person known not to have the certain condition is developed. This normal differential gene expression pattern will include the gene expression characteristics for a number of the genes likely to have different gene expression characteristics from the expression characteristics of those same genes from a body having the certain condition. Other particular genes that can provide other desired information regarding a body may also be included in the normal differential gene expression pattern, if desired. Once this normal differential gene expression pattern is developed, it can be used to screen or diagnose a patient to determine if the patient has the certain condition. To do this, a "patient differential gene expression pattern" is developed for the patient to be screened for the certain condition. The patient differential gene expression pattern will show the gene expression characteristics for the same genes as included in the normal differential gene expression pattern so that those gene expression characteristics can be compared. Significant differences between the patient differential gene expression pattern and the normal differential gene expression pattern indicates that the body from which the patient differential gene pattern was obtained is suffering from the certain condition. It has been found that the peripheral blood monocyte-lymphocytes gene system will begin to change as the condition in the body develops, thereby allowing much earlier diagnosis of the developing condition than with prior art methods of diagnosis. For example, with a developing neoplasm in a patient, such as a pancreatic tumor leading to ductal pancreatic adenocarcinoma, the patient's peripheral blood monocyte-lymphocyte's gene system recognizes and continues to react to the developing neoplasm. The developing changes in the tumor growth will be reflected in statistically significant differences in the peripheral blood monocyte-lymphocyte's gene expression patterns compared to normal peripheral blood monocyte-lymphocyte gene expression patterns in people known not to have the developing neoplasm. The normal differential gene expression pattern is generated from a group of people known not to be suffering from a developing neoplasm. Such group of people may be similar in age and gender, and/or other features, to the patient being screened, although matching age, gender, or other features appears not to be necessary. The comparison of the patient differential gene expression pattern with the normal differential gene expression pattern allows the early diagnosis of the developing neoplasm or disease.

By comparing the monocyte-lymphocyte gene expression characteristics of the monocyte-lymphocytes genes from the group of bodies having the certain known condition with the monocyte-lymphocyte gene expression characteristics of similar peripheral blood monocyte-lymphocytes from the group of bodies known not to have the certain condition, not only is the normal differential gene expression pattern typical of a person known not to be suffering from the certain condition developed, but a "condition differential gene expression pattern" typical of a person known to have the certain condition is also developed. Thus, although it is currently preferred to compare the patient differential gene expression pattern with the normal differential gene expression pattern to determine differences with the differences indicating the existence of the certain condition in the patient being screened, the patient differential gene expression pattern can be compared with the condition differential gene expression pattern to determine similarities between the patterns with the similarities between the patterns, rather than differences between the patterns, indicating the existence of the certain condition in the patient.

In developing the "normal differential gene expression pattern," the "condition differential gene expression pattern," and the "patient differential gene expression pattern," the gene expression characteristics determined for each pattern should be the same gene expression characteristics and such gene expression characteristics should be determined in a similar manner. A currently preferred method of determining the gene expression characteristics is with a gene expression microarray pattern. Such an array provides an indication of whether a gene is expressed neutrally, or whether the gene is over expressed or under expressed. In such case, it is the characteristics of over expression or under expression that are determined and compared.

While there are various ways of preparing the monocyte-lymphocyte genes for determination of the gene expression characteristics, a currently preferred method processes peripheral blood monocyte-lymphocytes isolated from blood drawn from a patient or other body to total RNA, and obtains amplified aRNA or cDNA from the total RNA. The separation of the monocyte-lymphocytes from the blood is preferably begun rapidly, within about two hours of drawing the blood, and more preferably within about twenty to thirty minutes of drawing the blood. The separated mononuclear cells are then preserved before storage or freezing. To determine the gene expressions, the aRNA or cDNA is hybridized to the microarray. The data obtained from the microarray is analyzed with available computer software for that purpose, such as Gene Sight software, with mean paired ratios using Universal Human Reference RNA as a standard, usually with a p value of 0.0001 or 0.00001 of over expressed or under expressed genes.

The separation of the monocyte-lymphocytes from the blood may involve separating and isolating subsets of CD8, CD4, and CD4-CD25 T lymphocytes and B lymphocytes from the blood. The subsets of CD8, CD4, and CD4-CD25 T lymphocytes and B lymphocytes can be obtained through negative selection of the cells which are then processed to total RNA with amplification of polyadenylated messenger RNA to amplified anti-sense aRNA or to cDNA. Use of negatively selected CD8, CD4, CD4-CD25 T lymphocytes and B lymphocytes isolated from the peripheral blood of persons with breast, lung, colon and pancreatic cancer and other disease conditions, as well a monitoring organ transplant donor and recipients before and after the transplant may provide a specific and more focused early diagnosis of the growth or patient's disease or transplant condition.

This invention will provide the identification of a number of particular genes of which the over expression or under expression thereof to a high degree of probability indicate the presence of breast, lung, colon and pancreatic growths and cancers, as well as monitoring donor and recipient organ transplant subjects for transplant rejection or the development of transplant related and unrelated conditions and diseases.

In a preferred method of preparing the monocyte-lymphocyte genes for determination of the gene expression characteristics, venous blood is drawn from a peripheral vein, usually an anti-cubital arm vein. The blood is drawn into an RNase free, heparinized vacuum tube with a Ficoll gradient. The blood specimens are immediately processed with centrifugation and aspiration of the mononuclear cell layer with sterile RNase free pipettes and RNase free laboratory equipment. This process is started within two hours of the drawing of the blood, and preferably within 20 to 30 minutes of the drawing of the blood. This mononuclear cell layer is then washed and preserved according to a careful and consistent protocol method. Further processing can be continued immediately or the preserved specimen can be stored at −80° C. for later processing. In the further processing, total RNA is extracted from the preserved cells and polyA messenger RNA from the total RNA is amplified to antisense aRNA or cDNA for subsequent hybridization to microarray human slides. Universal Human Reference RNA is similarly processed at that time for use as a reference standard.

The results of these microarray hybridization studies can be analyzed with the Gene Sight software using a Student's Test method. The individual genes are initially matched to the control specimen genes with a pair Mean ratio difference of p 0.00001 or p 0.0001. The patterns of selection are noted with the Hierarchical Cluster method. The individual genes over expressed and under-expressed in this comparison are recorded. Other methods of analysis can also be used, including the SAM method, a different linear ANOVA test method and other methods, including the ROC/AUC method.

DETAILED DESCRIPTION OF THE INVENTION

Figure 1:
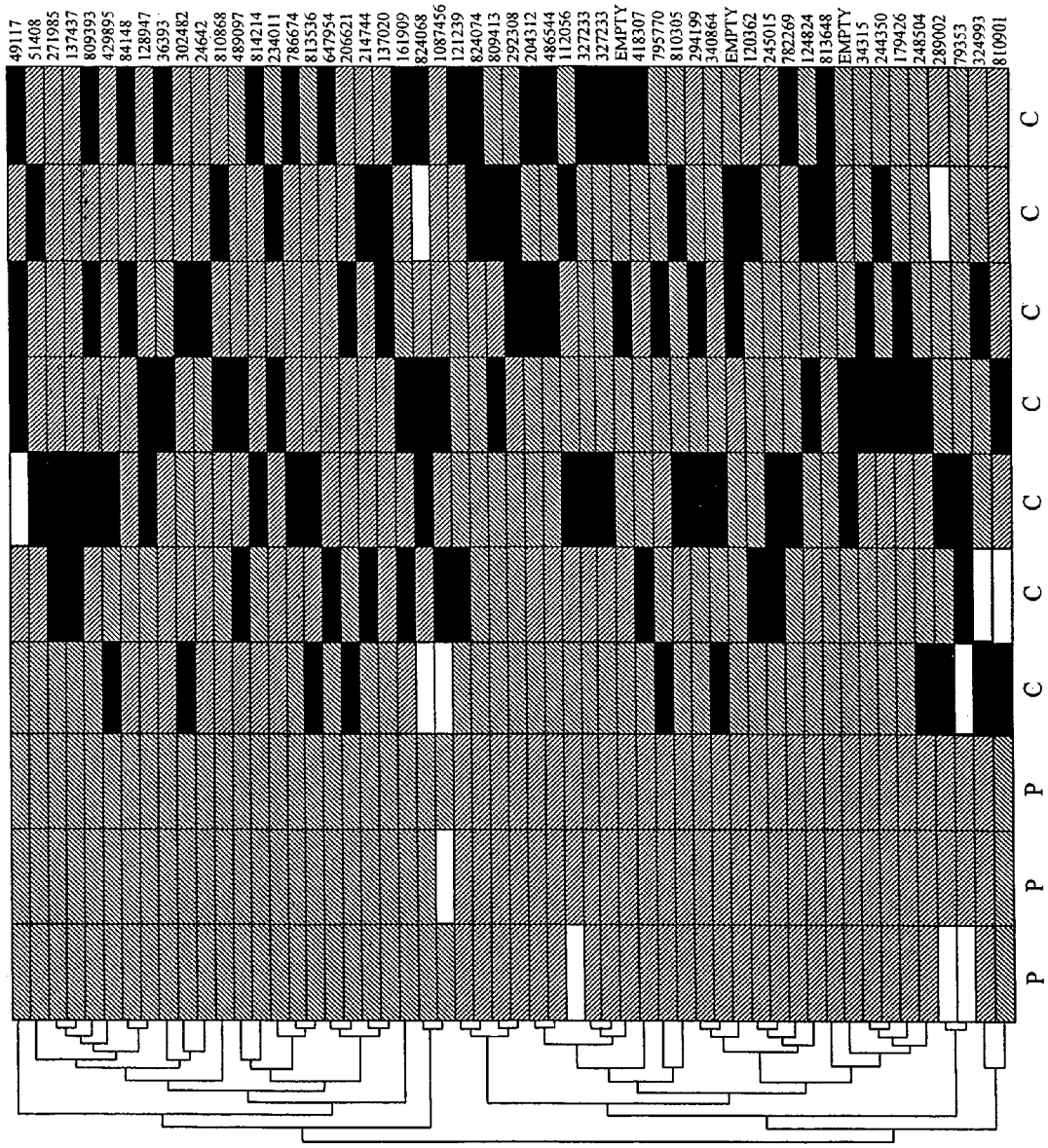
FIG. 1 is a showing of the results of microarray determination of gene expression characteristics of three patients with known ductal pancreatic adenocarcinoma and seven persons without ductal pancreatic adenocarcinoma used as controls or normals.

The invention, in part, involves obtaining gene expression characteristics of the gene system of monocyte-lymphocytes of the peripheral blood from a body or patient to be tested. This usually includes obtaining peripheral blood from the body or patient to be tested, separating or isolating the monocyte-lymphocytes from the blood, processing the monocyte-lymphocytes to allow determination of gene expression characteristics of the genes, and determining the gene expression characteristics of the genes. In a preferred method of obtaining and processing the monocyte-lymphocytes, a peripheral blood sample is obtained from the patient in the usual manner of obtaining venous blood from a peripheral vein, such as the anti-cubital vein of the arm. Usually 16 ml in two 8 ml tubes is drawn into sterile RNase free vacuum tubes with a Ficoll type gradient and heparin. (Such as the BD Vacutainer CPT tubes with heparin.) Although not the preferred method, other anticoagulants such as potassium ethylene-diamine tetra-acetic acid (EDTA) or sodium citrate may be used. These tubes are centrifuged at a centrifugal force of about 1500×g, using, for example, the top of the tubes 17 cm from the center of the center post of the centrifuge, for 20 minutes at 2800 rpm at room temperature. The resulting 'snow storm' of monocyte-lymphocytes sits on top of the Ficoll gradient and below the clear plasma layer. Approximately 2 ml of this monocyte-lymphocyte layer is aspirated with a sterile RNase free plastic Pasteur bulb tube and placed in a sterile RNase free 15 ml plastic tube with a screw top.

The cells in the aspirated sample are then washed one time. Approximately 13 ml of 1×PBS (phosphate buffered saline) solution made with RNase free water, is added to the plastic tube, and centrifuged at 1300 rpm for 15 minutes. The same distance is used for the centrifuge as previously, 17 cm from the center of the center post of the centrifuge. This is done at room temperature. A small white pellet is found at the bottom of the centrifuged 15 ml plastic tube. The supernatant is gently poured from the tube without disturbing the pellet. The small remaining part of the supernatant is very gently aspirated from the tube, again not disturbing the pellet.

The cells in the pellet are now preserved in one of three ways. In method A, two tubes with the pellets are used and 350 µl added of a B-ME (B-Mercapthanol) preservative. (Such as 10 µl of B-ME in 1 ml of Buffer RLT from the Quiagen RNeasy Mini Protect Kit.) Mild vortexing of the lysate with the pellets in the tube is gently done, holding the tube to the side of the rim of the vortexing machine. Allow the cells to be lysated for five or more minutes and draw back and forth through a sterile Rnase free # 18 needle and 1 ml sterile Rnase free syringe five times gently. This amount from the two pellets in the two tubes is then transferred to one 1.5 ml Eppendorff sterile RNase free tube. This may then be stored at −80° C. or continued to be processed to total RNA (tRNA). In method B, the sample may instead be placed in a DMSO (dimethyl sulphoxide) solution made up of 500 µl of DMSO, 500 µl of the patient's own serum and 4 ml of RPMI 1640 which is mixed and then 1 ml added to the pellet at the bottom of the 15 ml plastic tube and gently vortex. This may then be slowly frozen to −80° C. for storage or immediately processed to total RNA (tRNA). If it is stored at −80° C., it should be melted rapidly to 37° C. before processing to total RNA. This procedure allows the cells to be negatively selected to lymphocyte subsets of CD8, CD4, CD4-CD25 and B lymphocytes which are then processed to aRNA or to cDNA as described below for microarray pattern recognition. In method C, 100 µl of RNlater (from Qiagen RNeasy Mini Protect Kit) may instead be added to the washed pellet as a preservative to stop enzyme degradation. This is thought to be a high salt solution and the cells in this solution may not be effectively negatively selected for subset analysis. The patterns in this method (Method C) are of the total monocyte-lymphocyte gene expression reaction to the neoplasm.

If the B-ME buffered method of lysate of two tubes of pellets (Method A) is used for further processing to total RNA, an equal amount of 70% ethanol made from pure absolute alcohol with 30% of RNase free non-DEPCA treated sterile water added to the alcohol, is added to the cell containing lysate in the Eppendorff tube. This is gently mixed and then in 700 µl amounts added to a silica gel column. (Such as that supplied by Qiagen in their Mini Protect Kit.) This is then centrifuged at 10,000 rpm (approximately 9,000 g.) for one minute and the flow through discarded. The ethanol bounded total RNA with higher amount of messenger RNA (mRNA) is bound to the silica gel membrane which is then washed and eluted in sterile RNase free water. In more detail, the remaining lysate in the Eppendorff tube is transferred in 70 µl or less volume to the silica column and centrifuged in a microcentrifuge again for one minute at the same speed, 10,000 rpm. The flow through is discarded and 350 µl of a wash solution. (Such as that from the Qiagen RNeasy Mini Protect Kit). Is placed on the column and again centrifuged for one minute at 10,000 rpm. Following this add 10 µl of DNase1 stock solution from an RNase Free DNAse Set (Introvirogen) to 70 µl RDD buffer. This eliminates the remaining small amount of DNA leaving the enriched mRNA. Mix gently by inverting and add gently to the silica gel column. Let stand for 15 minutes then wash again with 350 µl of a wash solution, microcentrifuging for one minute at 10,000 rpm. Discard the flow through.

Pipette 500 µl of Buffer RPE from the Qiagen Kit to the column and centrifuge for one minute at 10,000 rpm using the same collection tube. Discard the flow through. Pipette another 500 µl of RPE Buffer solution (again to wash the column with ethanol) to the column with a new collection tube and centrifuge again for one minute at 10,000 rpm in a microcentrifuge. If the column is not totally dry, discard the flow through and recentrifuge at 16,000 rpm for one minute. Do not do this last step, if the column is dry.

Transfer the dry silica gel column to a new 1.5 m RNase free collection tube and pipette 30 µl of RNase free sterile water directly onto the silica gel membrane, holding the pipette only one or two millimeters above the membrane. Microcentrifuge the column at 10,000 rpm for one minute. This gives 30 µl of total RNA (tRNA). One may then OD (optical density with UV spectrophotometry) one µl of this, with or without dilution, to determine the concentration or quantity of total RNA (tRNA). One may also run a gel to be sure the bands indicate no degradation of the total RNA.

After the total RNA (tRNA) is measured for concentration by OD, amplification to aRNA or cDNA is carried out After the specimen is successfully bio-analyzed, hybridization to microarray is done to evaluate over and under expression of the genes.

The gene expression patterns will then be analyzed with advanced software to determine the statistically significant expression of the cancer or other disease conditions compared to the normal expected patterns of non-diseased control samples. 'Gene Sight' software with hierarchical clusters, statistical analysis of microarray 'SAM', a linear ANOVA method and other methods, including the ROC/AUC method, were used to analyze the microarray data in this determination of the significantly over expressed and under expressed genes distinguishing the cancers and other disease conditions from age and gender approximated controls without known disease. This method may also be used to monitor transplant donors and recipients before and after organ transplantation for organ rejection or other disease conditions related and unrelated to transplantation.

This method may be modified to increase the availability and reduce the laboratory time and cost of the test with the use of direct linear amplification of smaller amounts of total RNA to cDNA for direct attachment of dyes for microarray with different or hybrid promoters and primers (such as with the NuGene method). Also, this method may be enhanced by use with newer microfluid chips. Even more focused gene patterns may be evaluated with negatively selected combinations of subsets of the T and B lymphocytes for patterns of gene expression of early developing tumors or disease conditions, allowing early resection or destruction of the tumor before metastatic spread of the subsequent cancer and other methods of earlier control of the disease condition, as well as better control to the tolerance of the transplanted organ.

This method gives the patterns needed for the early diagnosis of the altered disease state and transplantation condition. This method describes one useful method of accomplishing the invention claimed in this patent of using the peripheral blood monocyte-lymphocytes for the early diagnosis of breast, lung, colon and pancreatic growths and cancers and other disease conditions, as well as the condition of donor and recipient organ transplants.

One hypothesis of this invention is that the peripheral blood lymphocyte microarray gene expression patterns will show a specific and unique identification of a breast, lung, colon or pancreatic cancer patient compared to the microarray gene expression patterns of informed volunteer age and gender approximated controls without this disease. To test this hypothesis, peripheral blood mononuclear cells were isolated from the peripheral blood specimens of patients and controls. The isolated mononuclear cells were estimated to consist of about 80% to about 95% lymphocytes. The venous blood was drawn from a peripheral vein, usually an anticubital arm vein, of informed and consenting patients with subsequent pathology proven tissue diagnosis of the studied disease. These specimens were from intraductal pancreatic adenocarcinoma patients who did not have treatment with radiation or chemotherapy prior to the obtaining of the blood specimens. The gene expressions from the processed blood specimens were analyzed and compared to similar drawn and processed specimens from age and gender approximated informed volunteer controls without the disease.

The blood was drawn into an RNase free, heparinized vacuum tube with a Ficoll gradient. The blood specimens were immediately processed with centrifugation and aspiration of the mononuclear cell layer with sterile RNase free pipettes and RNase free laboratory equipment. This process was started usually within 20 to 30 minutes of the drawing of the blood and certainly within 2 hours. This mononuclear cell layer was then washed and preserved according to a careful and consistent protocol described above. Further processing could be continued immediately or the preserved specimen could be stored at −80° C. for later processing.

As described above, total RNA was extracted from the preserved cells and polyA messenger RNA from the total RNA was amplified to antisense aRNA or cDNA for subsequent hybridization to microarray human slides. Universal Human Reference RNA was similarly processed at that time for use as a reference standard. The antisense aRNA or cDNA from the preserved cells from a specimen and the Universal Human Reference RNA antisense aRNA or cDNA was hybridized to microarray human microarray slides and the slides processed to show the gene expression characteristics of the genes from the respective blood specimens of patients with the studied cancer and controls without the studied cancer. The results of these microarray hybridization studies were analyzed with the Gene Sight software using a Student's Test method. As stated above, other methods of analysis were also used, including the SAM method, a different linear ANOVA method and other methods. The results from all methods were compared and the results from different patient's specimens were compared. The individual genes were often matched to the control specimen genes with a pair Mean ratio difference of p 0.00001 (one chance in 10,000 that the indicated over expression, neutral expression, or under expression was random) or p 0.0001 (one chance in 1,000 that the indicated over expression, neutral expression, or under expression was random) for selection with Gene Sight software. The patterns of selection were noted with the Hierarchical Cluster method and the individual genes over and under-expressed in this comparison were recorded. Cross-expression of these genes between methods and specimens are noted and recorded The Gene Sight or other software is then used to indicate the results in selected manners, such as in hierarchical clusters. The results obtained in this manner are colored charts showing the expression for individual genes in red if the gene is significantly over expressed, green if the gene is significantly under expressed, and black if there is no significant expression, referred to herein as neutral expression. These gene expression indications and charts for indicating gene expression are well known to those skilled in the art.

FIG. 1 shows the results of microarray determination of gene expression characteristics of three patients with known ductal pancreatic adenocarcinoma and seven persons without ductal pancreatic adenocarcinoma used as controls, and showing only gene expressions that have been determined to be different between patients with ductal pancreatic adenocarcinoma and controls without ductal pancreatic adenocarcinoma, at a p of 0.0001. FIG. 1 shows the results of a human slide A comparison, evaluating 9600 genes in duplicate. The first three columns from the left in FIG. 1, labeled at the bottom of each column as PA, show the gene expressions for the particular genes labeled for each row at the right side of the FIG. 1. The gene labels shown in FIG. 1 are the Image ID Numbers for the genes. Each column labeled PA represents a "patient differential gene expression pattern" as described earlier where the pattern is made up of the particular genes labeled on the right. The seven columns labeled C show the gene expressions for the particular indicated genes for the controls. Each column represents a differential gene expression pattern for a particular control. To generate a "normal differential gene expression pattern," a combination of all seven individual control column patterns would be generated. Similarly, to generate a "condition differential gene expression pattern," an average or other combination of all three individual patient column patterns would be generated. When printed in color, the greens and reds of some individual patterns sometimes vary in shade or intensity indicating the measured intensity of the over or under expression. However, in the black and white drawings of FIGS. 1-3, the red is indicated by diagonal lines sloping downwardly to the right and the green is indicated by diagonal lines sloping downwardly to the left. No indications are made to indicate intensity. The black indicates neutral intensity while the white or blank spaces indicate no measurement for that particular gene for that particular sample.

FIG. 1 shows particular genes that exhibit different expression between the patients with ductal pancreatic adenocarcinoma and the controls without ductal pancreatic adenocarcinoma. This data shows distinct patterns of gene expression microarrays on human slides A separating ductal pancreatic adenocarcinoma patients prior to treatment compared to age and gender approximated controls.

Figure 2:
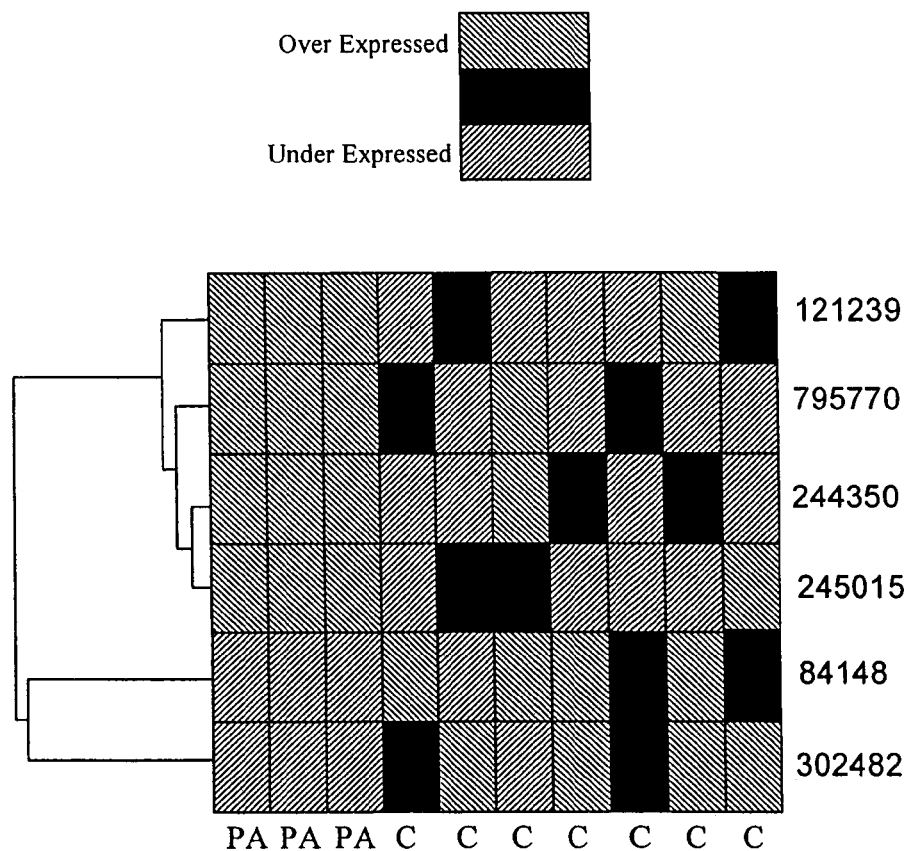
FIG. 2, a showing similar to that of FIG. 1 of the results of microarray determination of gene expression characteristics of three patients with known ductal pancreatic adenocarcinoma and seven persons without ductal pancreatic adenocarcinoma used as controls, but to a higher probability of certainty than shown in FIG. 1.

FIG. 2 shows the results of microarray determination of gene expression characteristics for the same three patients with known ductal pancreatic adenocarcinoma and the same seven persons without ductal pancreatic adenocarcinoma used as controls, as shown in FIG. 1. However, FIG. 2 shows only gene expressions that have been determined for particular genes to be different between patients with ductal pancreatic adenocarcinoma and controls without ductal pancreatic adenocarcinoma, at a p of 0.00001 rather than 0.0001 (only one chance in 10,000 that the indicated over expression, neutral expression, or under expression was random as opposed to one chance in 1,000). Thus, the difference of these particular genes, which are also included in the genes shown in FIG. 1, between a patient and a normal have a higher degree of indicating the presence of ductal pancreatic adenocarcinoma than the other genes shown on FIG. 1.

Figure 3:
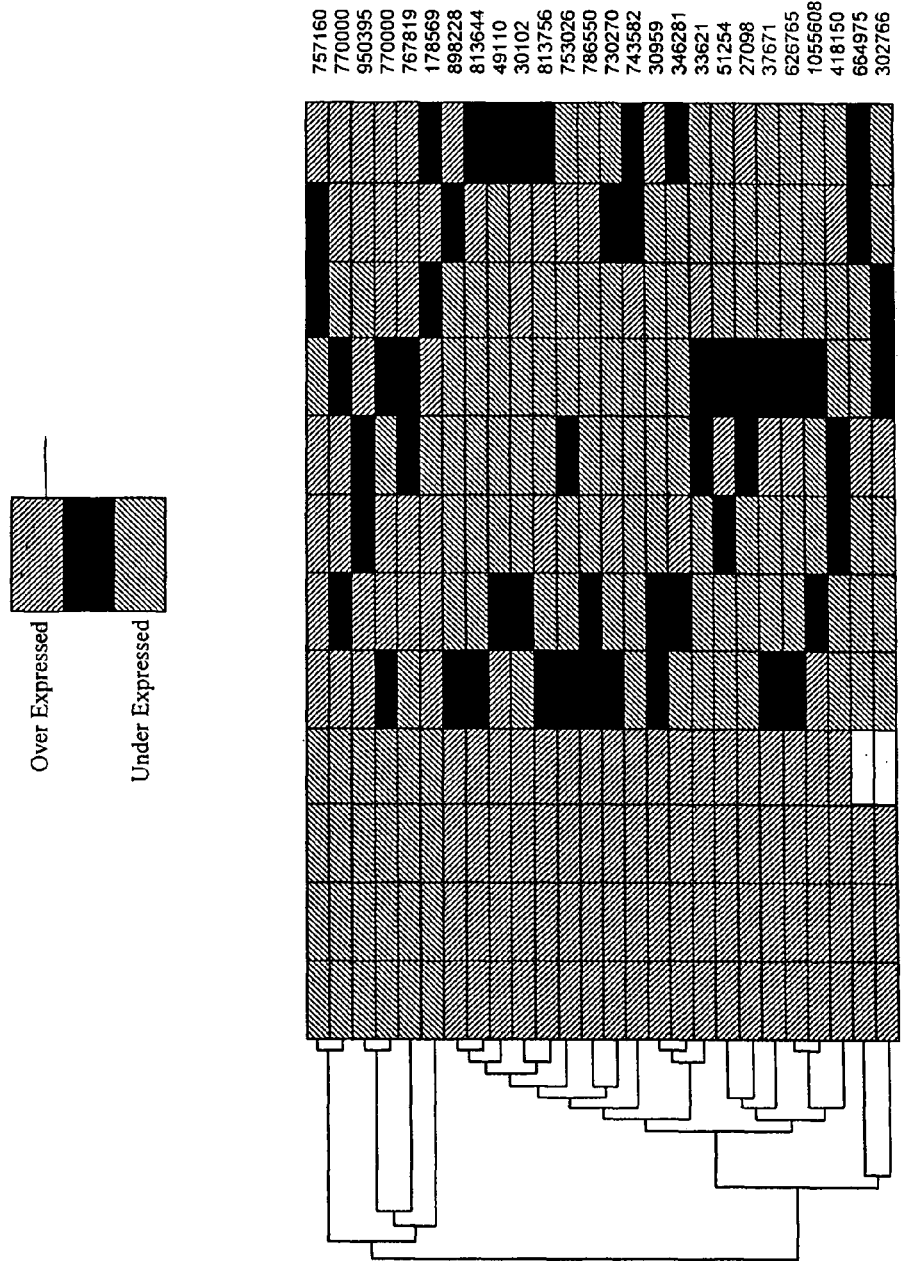
FIG. 3, a showing of the results of microarray determination of gene expression characteristics of four patients with known ductal pancreatic adenocarcinoma and eight persons without ductal pancreatic adenocarcinoma used as controls or normals.

FIG. 3 shows the results of microarray determination of gene expression characteristics of four patients with known ductal pancreatic adenocarcinoma and eight persons without ductal pancreatic adenocarcinoma used as controls, and showing only gene expressions that have been determined to be different between patients with ductal pancreatic adenocarcinoma and controls without ductal pancreatic adenocarcinoma, at a p of 0.00001, similar to the p of FIG. 2. FIG. 3 shows the results of a human slide B comparison of 9600 different genes in duplicate. The first four columns from the left in FIG. 3, labeled at the bottom of each column as PA, show the gene expressions for the particular genes labeled for each row at the right side of the FIG. 1. The eight columns labeled C show the gene expressions for the particular indicated genes for the controls. FIG. 3, shows distinct patterns of gene expression microarrays with human slide B separating ductal pancreatic adenocarcinoma patients prior to treatment compared to age and gender approximated controls.

The genes identified by Image ID Numbers in FIGS. 1-3 were further identified using the Oncogenomics and NCBI data reference sources listed as follows:

A. Oncogenomics, Pediatric Oncology Branch, CCR, NCI, NIH, DHHS.

B. National Center for Biotechnology Information (NCBI)

National Library of Medicine (NLM)

National Institutes of Health (NIH)

Sequence listing for the particular genes, where available, may be found on one of these sites using the identification for the gene provided here. Information regarding the identified genes available on these web sites is incorporated herein by reference.

For example, the first four genes listed below were found to be significantly over expressed and the next two genes under expressed in the ductal pancreatic adenocarcinoma patients peripheral blood mononuclear cells, when compared to age and gender approximated controls, constituting a pattern of recognition of pancreatic cancer as compared to the gene expression patterns in those without pancreatic cancer

| Gene Symbol | Gene Name Image ID # | Gene # | Unigene Cluster (Locus Link) |
|---|---|---|---|
| 1. SOC | Socius ID#121239 | G#91544 | Hs145061 |
| 2. C1orf38: | Chromosome 1 open reading frame 38 ID#307255 | G#9473 | Hs10649 |
| 3. BCL6 | B cell CLL lymphoma 6 (zinc finger protein 51) ID#201727 | G#8067 | Hs155024 |
| 4. LTBR | lymphotoxin beta receptor (TNFR superfamily, member 3) ID#811900 | G#4055 | Hs1116 |
| 5. | HomoSapians p38 beta 2 MAP kinase mRNA, completeCDS ID#84148 | | |
| 6. SLC9A3R2: | solute carrier family 9(sodium hydrogen exchanger), isoform 3 regulater 2. ID#178569 | | Hs 440896 |

For example, when several of the fourteen genes listed below, are over-expressed in the peripheral blood mononuclear cells, they are most likely to express a pattern diagnostic of intraductal pancreatic adenocarcinoma. If two or more of the first 9 genes listed below are found to be over-expressed in the peripheral blood mononuclear cells, one should consider careful evaluation of the patient for the presence of a pancreatic tumor. If three or more of these first listed 14 genes are found to be expressed in an elevated state one should very carefully evaluate the patient for the presence of intraductal pancreatic adenocarcinoma.

For example, the following 7 genes numbered 15 through 21 are most likely to form an under-expressed pattern in the diagnosis of intraductal pancreatic adenocarcinoma, as illustrated on the hierarchical cluster illustration examples of FIGS. 1-3. When one or more of these under-expressed genes is combined with the patterns of the first listed 14 over-expressed genes listed above the patient should be clinically very carefully evaluated for intraductal pancreatic adenocarcinoma.

| Gene Symbol | Gene Name Image ID # | Gene # | Unigene Cluster (Locus Link) |
|---|---|---|---|
| 1. SOC | Socius ID#121239 | G#91544 | Hs145061 |
| 2. C1orf38: | Chromosome 1 open reading frame 38 ID#307255 | G#9473 | Hs10649 |
| 3. LIMD1: | LIM domain containing 1 ID#795770(757350) | G#8994 | Hs193370 |
| 4. ESTs | ID#244350 | | Hs47868 |
| 5. UBAP2L(NICE4) | Ubiquitin associated protein 2-Like. (NICE4 protein) ID#245015 | G#9898 | Hs8127 |
| 6. NUP93 | Nucleoporin 93 kDA ID#51918 | G#9688 | Hs 295014 |
| 7. BCL6 | B cell CLL lymphoma 6 (zinc finger protein 51) ID#201727 | G#8067 | Hs155024 |
| 8. EST | ID#564126 | | (Hs6716) |
| 9. LTBR | lymphotoxin beta receptor (TNFR superfamily, member 3) ID#811900 | G#4055 | Hs1116 |
| 10. MYC | V-myc myctocytomatosis viral oncogene homolog (avain) ID#812965 (417226) | G#4609 | Hs202453 |
| 11. RB1CC1 | RB1-inducible coiled - coil 1 (*Homo Sapiens*) ID#23431 | G#9821 | Hs151202 |
| 12. SELL | selretin L (lymphocyte adhesion molecule 1) ID#149910 | G#6402 | Hs82848 |
| 13. LCP2 (SLP-76) | lymphocyte cytosolic protein 2 ID#415127(283715) | G#3937 | Hs2488 |
| 14. PRG1 | Proteoglycan 1, secretin granule ID#415021(703581) | G#5552 | Hs1908 |

| 15. | | HomoSapians p38 beta 2 MAP kinase mRNA, completeCDS ID#84148 | |
| --- | --- | --- | --- |
| 16. | | Prostacyclin-stimulating factor] human, cultured diplid fibroblast co ID#302482 | Hs119206 |
| 17. | SLC9A3R2: | solute carrier family 9(sodium hydrogen exchanger), isoform 3 regulater 2. ID#178569 | Hs440896 |
| 18. | EST | Transcribed sequence ID#757160 | Hs480744 |
| 19. | | Transcribed sequences with moderate similarity to protein vet: NP_115737.1 homo sapiens hypothetical protein MGC 5469 ID#950395 | Hs 509207 |
| 20. | EP400: | E1A binding protein p400 (CAGH32) ID377000 | Hs507307 |
| 21. | IQSEC1: | IQ motif and Sec7 domain 1 ID#767879 | Hs475506 |

For example, the 68 genes listed in Table 2 are the specific activated over-expressed and under-expressed genes in the peripheral blood mononuclear cells, consisting mostly of lymphocytes, in a specific response to intraductal pancreatic adenocarcinoma. The patterns of expression of these activated genes recorded on microarray will allow the diagnosis of intraductal pancreatic adenocarcinoma.

The patterns of difference as seen in the Hierarchal Clusters (FIGS. 1-3) between the pancreatic carcinoma patients and the controls reinforces the concept of a unique specific reaction of the various types of lymphocytes in the peripheral blood to the developing tumor, as one would expect from the TIL cell reaction with infiltration of specific lymphocytes to the tumor site. With one questionable exception *, these genes are not the genes noted in the peripheral blood mononuclear cells by Twine & Burczynski. Twine N C, et al. *Disease-associated expression profiles in peripheral blood mononuclear cells from patients with advanced renal cell carcinoma*. Cancer Res. 2003 Sep. 15; 63(18):6069-75. Burczynski M E, Twine N C et al. *Transcriptional profiles in peripheral blood mononuclear cells prognostic of clinical outcomes in patients with advanced renal cell carcinoma*. Clinical Cancer Res. 2005 Feb. 1; 11(3):1181-9, with melanoma by Xu. Xu T et al *Microarray analysis reveals differences in gene expression of circulating CD8+ T cells in melanoma patients and healthy donors*. Cancer Res. 2004 May 15; 64(10):3661-7 or by Hong. Hong M H, X. X., Mai H Q, Cao S M Min H Q, *Analysis of gene expression patterns of periphery lymphocytes in patients with nasopharyngeal carcinoma*. Ai Zheng, 2002. 21(1): p. 21-4. with naso-pharyngeal carcinoma; mitigating against a universal common generic gene expression reaction of the lymphocytes to all cancers and reinforcing the hypothesis of a specific recognition of the intraductal pancreatic adenocarcinoma by these lymphocytes. This method and concept can be applied to breast, lung, colon growths and cancers as well as to other pancreatic tumors and diseases. It also may be applied to the evaluation and treatment of the condition and conditions of donor and recipient organ transplants both before and after the organ transplantation. The evaluation of negatively selected subsets of peripheral blood lymphocytes such as CD8, CD4, CD4CD25 T lymphocytes and B lymphocytes may give a more precise and specific reacting gene expression pattern to the growing and changing tumor as it progresses. The use of pattern recognition rather than individual gene expression as a marker offers the advantage of countering the inherent variability in biological samples. Pattern recognition by combining the results of other tests, including proteomic SELDI-TOF patterns. Bhattacharyya S. Siegel E R, Peteresen G M, Chari S T, Suva L J, Haun R S. *Diagnosis of pancreatic cancer using serum proteomic profiling* Neoplasia. 2004 September-October 6(5): 674-86 and the use of specific methylation markers Herman J G, Baylin S B Gene silencing in cancer in association with promoter hypermethylation. N Engl J. Med. 2003 Nov. 20: 349(21): 2042-54. together, will further focus and elucidate the presence of a developing tumor and its response to modes of therapy.

(* Pyridoxal (pyridoxine, vitamin B6) kinase—noted on the original paper of Twine, et al. and on the linear ANOVA test of intraductal pancreatic adenocarcinoma only, but with different Hs. Identification.)

TABLE 1

| 31 LISTED GENES ||||
| --- | --- | --- | --- |
| Gene Symbol | Gene Name Image ID # | Gene # (Locus Link) | Unigene Cluster |
| 1. SOC | Socius ID#121239 | G#91544 | Hs145061 |
| 2. C1orf38: | Chromosome 1 open reading frame 38 ID#307255 | G#9473 | Hs10649 |
| 3. LIMD1: | LIM domain containing 1 ID#795770(757350) | G#8994 | Hs193370 |
| 4. ESTs | ID#244350 | | Hs47868 |
| 5. UBAP2L(NICE4) | Ubiquitin associated protein 2-Like. (NICE4 protein) ID#245015 | G#9898 | Hs8127 |
| 6. NUP93 | Nucleoporin 93 kDA ID#51918 | G#9688 | Hs 295014 |

TABLE 1-continued

31 LISTED GENES

| Gene Symbol | Gene Name<br>Image ID # | Gene # | Unigene Cluster<br>(Locus Link) |
|---|---|---|---|
| 7. ZNF313 | Zinc finger protein 313<br>ID#487165 | G#55905 | Hs 144949 |
| 8. PRUNE | Prune Homolog (*Drosphila*, *Homo Sapiens*)<br>(HTCD37 TcD37 homolog 58497)<br>ID#364324 | G#149428 | Hs78524<br>(Hs78524) |
| 9. FLJ12584 | Hypothetical protein FLJ12584<br>ID#269293 | G#80210 | Hs471610 |
| *10. PDXK | pyrdoxal (pyridoxine, vitamin B6)<br>(C21orf124 chromosome 21 open reading frame 124)<br>ID#590640 | G#8566 | Hs284491 |
| 11. MYC | V-myc myctocytomatosis viral oncogene homolog (avain)<br>ID#812965 (417226) | G#4609 | Hs202453 |
| 12. RB1CC1 | RB1-inducible coiled - coil 1 (*Homo Sapiens*)<br>ID#23431 | G#9821 | Hs151202 |
| 13. NKG7 | natural killer cell group 7 sequence<br>ID#71606 | G#4818 | Hs10306 |
| 14. SELL | selectin L (lymphocyte adhesion molecule 1)<br>ID#149910 | G#6402 | Hs82848 |
| 15. LCP2 (SLP-76) | lymphocyte cytosolic protein 2<br>ID#415127(283715) | G#3937 | Hs2488 |
| 16. BCL6 | B cell CLL lymphoma 6 (zinc finger protein 51)<br>ID#201727 | G#8067 | Hs155024 |
| 17. EST | ID#564126 | | (Hs6716) |
| 18. LTBR | lymphotoxin beta receptor (TNFR superfamily, member 3)<br>ID#811900 | G#4055 | Hs1116 |
| 19. PRG1 | Hematopoetic proteoglycan 1, secretory granule<br>ID#415021 (703581) | G#5675 | Hs1908 |
| 20. Serpine 1: | (PAL1): Plasminogen - activation inhibitor type 1<br>ID#589458 | G# 24617 | Hs82085 |
| 21. EDN 1: | Endothelin<br>ID#549409 | G#1906 | Hs2271 |
| 22. | (*Homo sapiens* chromosome associated protein - ECLAP-E mRNA complete c)<br>ID#66638 | | |
| 23. PBEF1: | Human pre-B cell enhancing factor (PBEF) mRNA, complete cds 10135<br>ID#488548 | | Hs154968 |
| 24. FPR1: | formyl peptide receptor 1<br>ID#773236 | G#2357 | Hs753 |
| 25. FLJ 31978: | hypothetical protein FLJ 31978<br>ID#809504 | G#144423 | Hs 12381 |
| 26. BNC2 | basonuclin 2<br>ID#344036 | G#54796 | Hs103853 |
| 27. MAST3 (KIAA0561) | microtubule associated serine/threonine kinase 3<br>ID#203350 | G#23031 | Hs173864 |
| 28. LOC113330 | hypothetical gene supported by NM 005631<br>ID#113330 | | |
| 29. | (LOC487647 similar to hypothetical protein FLJ21128)<br>ID#487647 | | |
| 30. EST (ZGC86904) | ZGC86904 (*dario revio*) (ZDB-GENE-040625)<br>ID#415186 | | Hs64906 |
| 31. EST | moderately similar to WW domain binding protein 1 (*M. musculus*)<br>(cbp A curved DNA binding protein)<br>ID998681 | | Hs7709 |

TABLE 2

The 68 genes in this table are the specific activated over-expressed and under-expressed genes in the peripheral blood mononuclear cells, consisting mostly of lymphocytes, in a specific response to intraductal pancreatic adenocarcinoma. The patterns of expression of these activated genes recorded on microarray will allow the diagnosis of intraductal pancreatic adenocarcinoma.

| Gene Symbol | Gene Name<br>Image ID # | Gene # | Unigene Cluster<br>(Locus Link) |
|---|---|---|---|
| 1. BCL6 | B-cell CLL/lymphoma-6 (Zinc finger protein 51)<br>ID# 201727 | G#604 | Hs155024 |
| 2. SOC | Socius<br>ID#121239 | G#91544 | Hs145061 |
| 3. C1orf38: | Chromosome 1 open reading frame 38<br>ID#307255 | G#9473 | Hs10649 |
| 4. LIMD1: | LIM domain containing 1<br>ID#757350 | G#8994 | Hs193370 |

TABLE 2-continued

The 68 genes in this table are the specific activated over-expressed and under-expressed genes in the peripheral blood mononuclear cells, consisting mostly of lymphocytes, in a specific response to intraductal pancreatic adenocarcinoma. The patterns of expression of these activated genes recorded on microarray will allow the diagnosis of intraductal pancreatic adenocarcinoma.

| Gene Symbol | Gene Name<br>Image ID # | Gene # | Unigene Cluster<br>(Locus Link) |
|---|---|---|---|
| 5. ESTs | ID#244350 | | Hs47868 |
| 6. UBAP2L(NICE4) | Ubiquitin associated protein 2-Like.<br>(NICE4 protein)<br>ID#245015 | G#9898 | Hs8127 |
| 7. IGA9 | Integrin, alpha 9<br>(weakly similar to CCAAT Box - BINDing transcript factor 1)<br>ID#898288 | G#3680 | Hs222 |
| 8. NR6A1 | Nuclear receptor subfamily 6, group A, number 1<br>ID#743582 | G#2649 | Hs 195161 |
| 9. LMCD1 | LIM and cysteine-rich domain 1<br>ID#786550 | G#29995 | Hs279943 |
| 10. SYN2 | Synapsin II<br>ID#51254 | G#6854 | Hs445503 |
| 11. FGD4 | FYVE, Rho GEF and PH domain containing 4<br>ID#730270 | G#121512 | Hs409311 |
| 12. | Transcribed sequences<br>ID#30959 | G#23283 | Hs12700 |
| 13.ESTs | (Moderately similar to Munc 13 [*H. Sapiens*])<br>ID#1055608 | | Hs112921 |
| 14. AP1S2 | Adaptor-related protein complex 1, Sigma 1 subunit 2<br>ID#813756 | G#8905 | Hs40368 |
| 15. PB1 | Polybromo 1<br>ID#813644 | G#55193 | Hs 173220 |
| 16. PARD3 | Par-3 partitioning defective 3 homolog (*C. elegans*)<br>(Transcribed sequence)<br>ID#753026 | G#56288 | Hs98872 |
| 17. CDNA | FLJ20913F13cloneADSEOO630<br>ID#49110 | | Hs7063 |
| 18.EST | Transcribed locus<br>ID#30102 | | Hs21169 |
| 19. ZD73D05 | Full length insert cDNA clone ZD73D05<br>ID#346281 | | Hs134314 |
| 20. KIAA0789: | KIAA0789 gene product.<br>ID#33621 | G#9671 | Hs158319 |
| 21. E2IG4 | hypothetical protein estradiol-induced<br>ID27098 | G#25987 | Hs8361 |
| 22. C18orf11 | Chromosome 18 open reading frame 11<br>ID#37671 | G#64762 | Hs12727 |
| 23. ESTs | transcribed locus.<br>ID#626765 | | Hs 537583 |
| 24. RAMP: | RA-regulated nuclear matrix associated protein<br>ID#418150 | G#51514 | Hs126774 |
| 25. CLDN1: | claudin 1<br>ID#664975 | G#9076 | Hs7327 |
| 26. FAM38B: | Family with sequence similarly 38 member B.<br>ID#302766 | G#63895 | Hs293907 |
| 27.CDNA | FLJ144273 fis, clone TOVAR 2001281<br>ID#241900 | G#389011 | Hs142074 |
| 28. ESTs | ID#139883 | | Hs28501 |
| 29. VNN3 | vanin 3<br>ID#120544 | G#55350 | Hs183656 |
| 30. EST | ID#485827 | | Hs45033 |
| 31. SLC1A7 | Solute carrier family 1 (glutamate transporter) member 7<br>ID#276515 | G#6512 | Hs104637 |
| 32. ALCAM: | Activated leukocyte cell adhesion molecule<br>ID#686180 | (G#214?) | Hs10247[Hs150693?] |
| 33. SLC22A3: | solute carrier family 22 (extraneuronal monamine transporter, member 3)<br>ID#127120 | G#6581 | HS242721 |
| 34. CD44? | ID#530788 | | Hs169610 |
| 35. EST | ID#564126 | | Hs6716 |
| 36. LTBR: | lymphotoxin beta receptor (TNFR superfamily, member 3)<br>ID#811900 | G#4055 | Hs1116 |
| 37. MRNA | cDNA DKFZp434D0818 (from cloneDKFZp434D0818)<br>ID#308478 | | Hs 5855 |
| 38. CD59: | antigen p18–20 (antigen identification by monoclonal antibodies<br>16.3A5, EJ16, EJ30, EL32 andG344)<br>ID#208001 | G#966 | Hs 278573 |
| 39. BBX: | Bobby sox homolog (*Drosophila*)<br>ID#503691 | G#56987 | Hs35380 |
| 40. NR6A1: | Nuclear receptor subfamily 6, group A, member1<br>ID#258666 | G#2649 | Hs195161 |

TABLE 2-continued

The 68 genes in this table are the specific activated over-expressed and under-expressed genes in the peripheral blood mononuclear cells, consisting mostly of lymphocytes, in a specific response to intraductal pancreatic adenocarcinoma. The patterns of expression of these activated genes recorded on microarray will allow the diagnosis of intraductal pancreatic adenocarcinoma.

| Gene Symbol | Gene Name Image ID # | Gene # | Unigene Cluster (Locus Link) |
|---|---|---|---|
| 41. | HomoSapians p38 beta 2 MAP kinase mRNA, completeCDS ID#84148 | | |
| 42. | Hs119206 Prostacyclin-stimulating factor] human, cultured diplid fibroblast co ID#502482 | | |
| 43. SLC9A3R2: | solute carrier family 9(sodium hydrogen exchanger), isoform 3 regulater 2. ID#178569 | G#9351 | Hs 440896 |
| 44. EST | Transcribed sequence ID#757160 | | Hs480744 |
| 45. | Transcribed sequences with moderate similarity to protein vet: NP_115737.1 *homo sapiens* hypothetical protein MGC 5469 ID#950395 | | Hs 509207 |
| 46. EP400: | E1A binding protein p400 G#57634 Hs507307 (CAGH32) protein EP400: E1A binding protein p400 AA427519 ID#377000 | | |
| 47. IQSEC1: | IQ motif and Sec7 domain 1 G# 9922 Hs475506 IQSEC1: IQmotif and Sec7 domain 1. AA418726 ID#7678791 | | |
| 48 LPHN2: | Lactrophilin 2 ID#346583 | G#23266 | Hs24212 |
| 49. PHF10: | PHD finger protein 10 *Homo Sapiens* ID#138589 | G#55274 | Hs435933 |
| 50. ZCCHC11: | Zinc finger, CCHC domain containing 11 ID#785963 | G#23318 | Hs528341 |
| 51. FLJ14775: | Hypothetical protein FLJ14775 ID#194023 | G#84923 | Hs103555 |
| 52. TRIM37: | Tripartite motif-containing 37 *Homo Sapiens* ID#305520 | G#4591 | Hs80667 |
| 53. DHX34: | DEAH (Asp-Glu-Ala-His) box polypeptide 34 ID#739990 | G#9704 | Hs151706 |
| 54. EST | ID#129624 | | Hs22031 |
| 55. EST | Transcribed sequence ID#124052 | | Hs226284 |
| 56. FLJ00133 | FLJ00133 protein ID#341641 | G#25992 | Hs471834 |
| 57. MGC15407 | similar to RIKEN cDNA4931428D14 ID#364873 | G#112942 | Hs23128 |
| 58. SPTAI: | spectrin, alpha, errthrocytic 1 (elliptocytosis 2) ID#204774 | G#6078 | Hs418378 |
| 59. SLC26A2: | solute carrier family 26 (sulfate transporter) member 2 ID#322537 | G#1836 | Hs302738 |
| 60. NVP160 | nucleoporin 160 kDa ID#33299] | G#23279 | Hs22559 |
| 61. | ID#48772] | | |
| 62. FPR1: | formyl peptide receptor 1 ID#773236 | G#2357 | Hs753 |
| 63. Serpine 1: | (PAL1): Plasminogen - activation inhibitor type 1 ID#589458 | G#24617 | Hs82085 |
| 64. EDN1: | Endothelin ID#549409 | G#1906 | Hs2271 |
| 65. FLJ 31978: | hypothetical protein FLJ 31978 ID#809504 | G#144423 | Hs 12381 |
| 66. PRGI: | Hematopoetic protoglycan core protein ID#415021(703581) | G#5552 | Hs1909 |
| 67. SMC2L1: | structural maintaince of chromosome 2 (*Homo sapiens* chromosome associataed protein - ECLAP-E mRNA complete c) ID#66638 | G#10592 | Hs119023 |
| 68. PBEF1: | Human pre-B cell enhancing factor (PBEF) mRNA, complete cds ID#488548 | G#10135 | Hs154968 |

Once particular genes are identified to look at for particular conditions, i.e., the particular genes are identified for a normal differential gene expression pattern for a particular condition or for a condition differential gene expression pattern for a particular condition which identifies the particular genes to be looked at for either differences or similarities to determine if a person is suffering from the particular condition, microarrays can be configured to provide only information on the particularly identified genes, i.e., to create the patient differential gene expression pattern. Thus, for screening for pancreatic cancer, a microarray could be configured to determine the expression for the patient to be screened of the particular genes identified in Table 1 or in Table 2 and a patient could be screened by looking at the expression for only those particular genes. The patient differential gene expression pattern would be generated by the microarray and then compared with either the normal differential gene expression for differences or the condition differential gene expression pattern for similarities to determine if the patient was likely to be suffering from the condition. The selected genes may be identified by a polymerase chain reaction (PCR) platform or specific gene chip, including a micro-fluid gene chip, without the use of the microarray platform.

Figure 4:
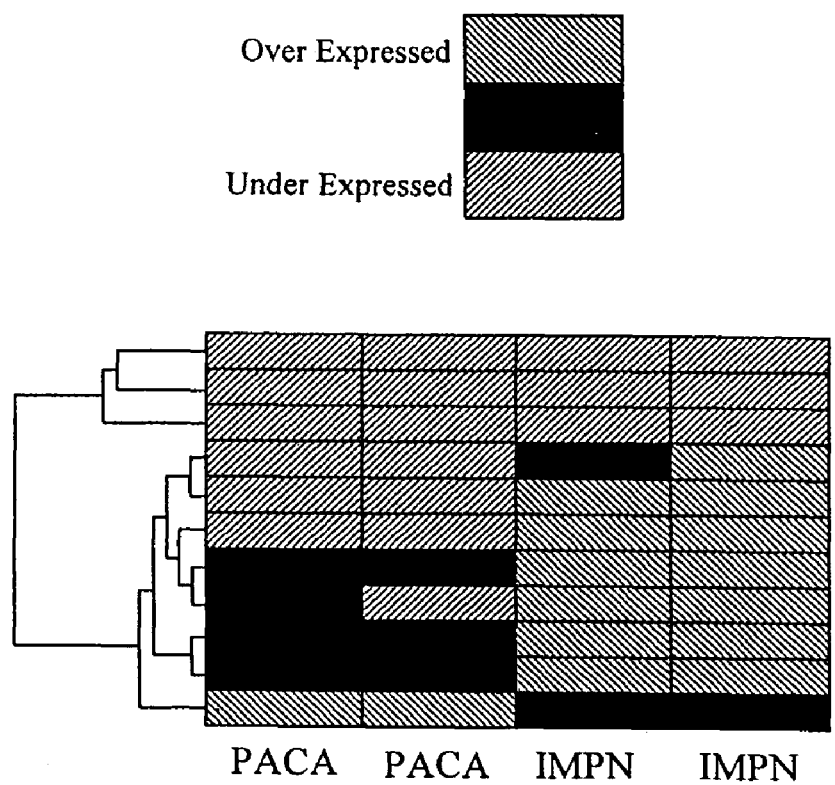
FIG. 4, a showing of the results of microarray determination of gene expression characteristics of two patients with known ductal mucinous pancreatic neoplasm and two persons with ductal pancreatic adenocarcinoma.
Figure 5:
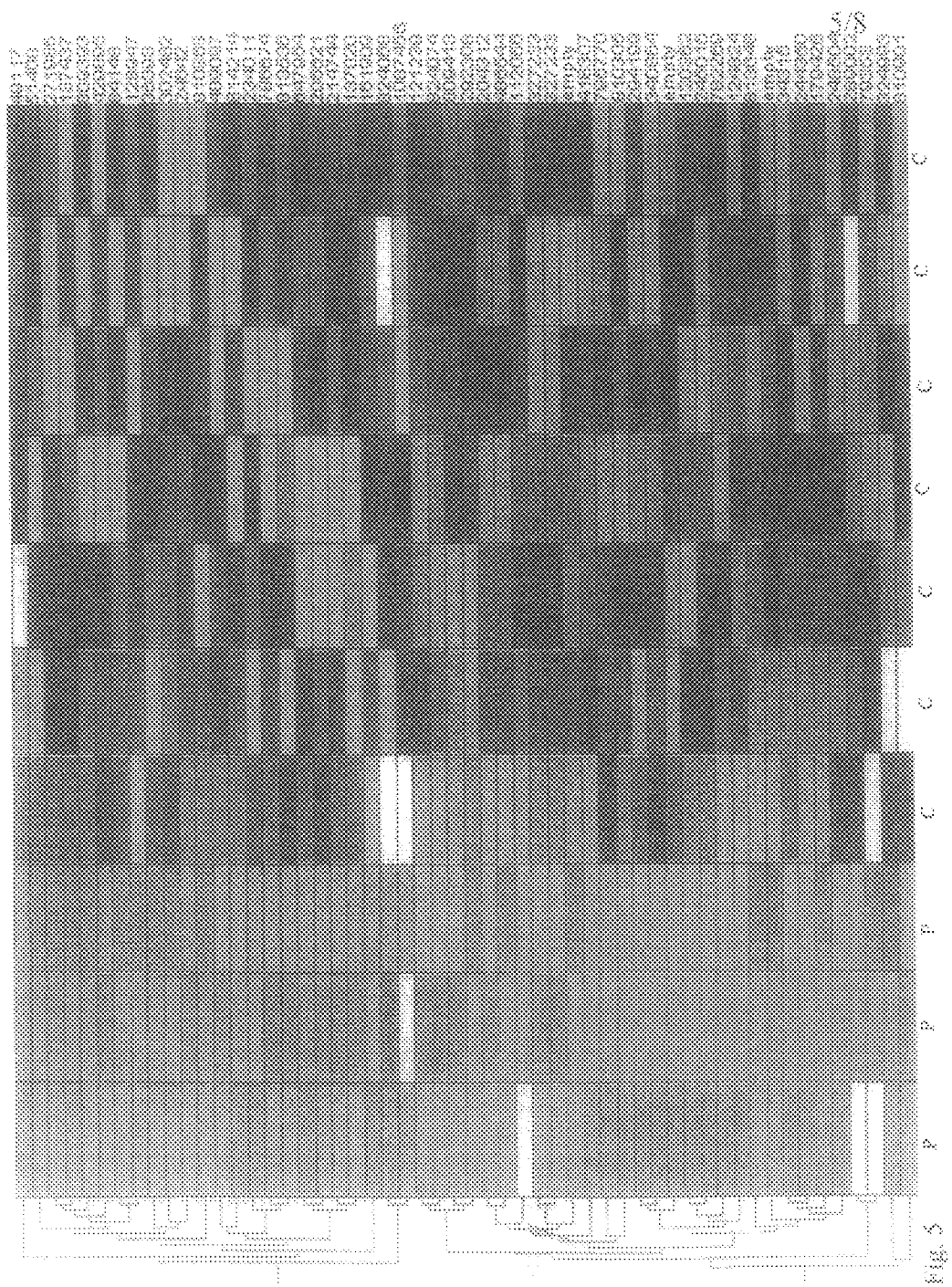
FIG. 5, the showing of the results of microarray determination of gene expression characteristics of FIG. 1, executed in color.
Figure 6:
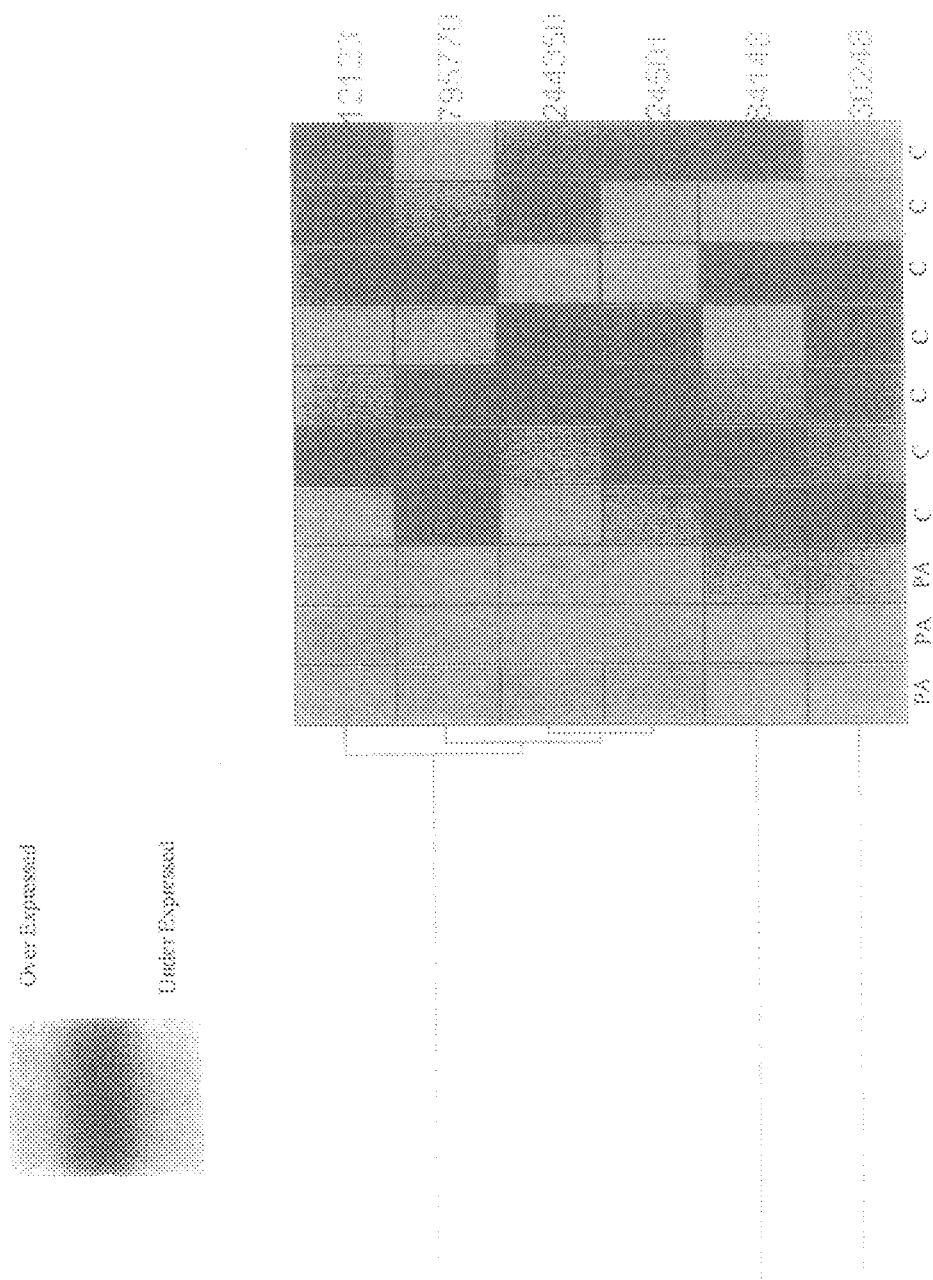
FIG. 6, the showing of the results of microarray determination of gene expression characteristics of FIG. 2, executed in color.
Figure 7:
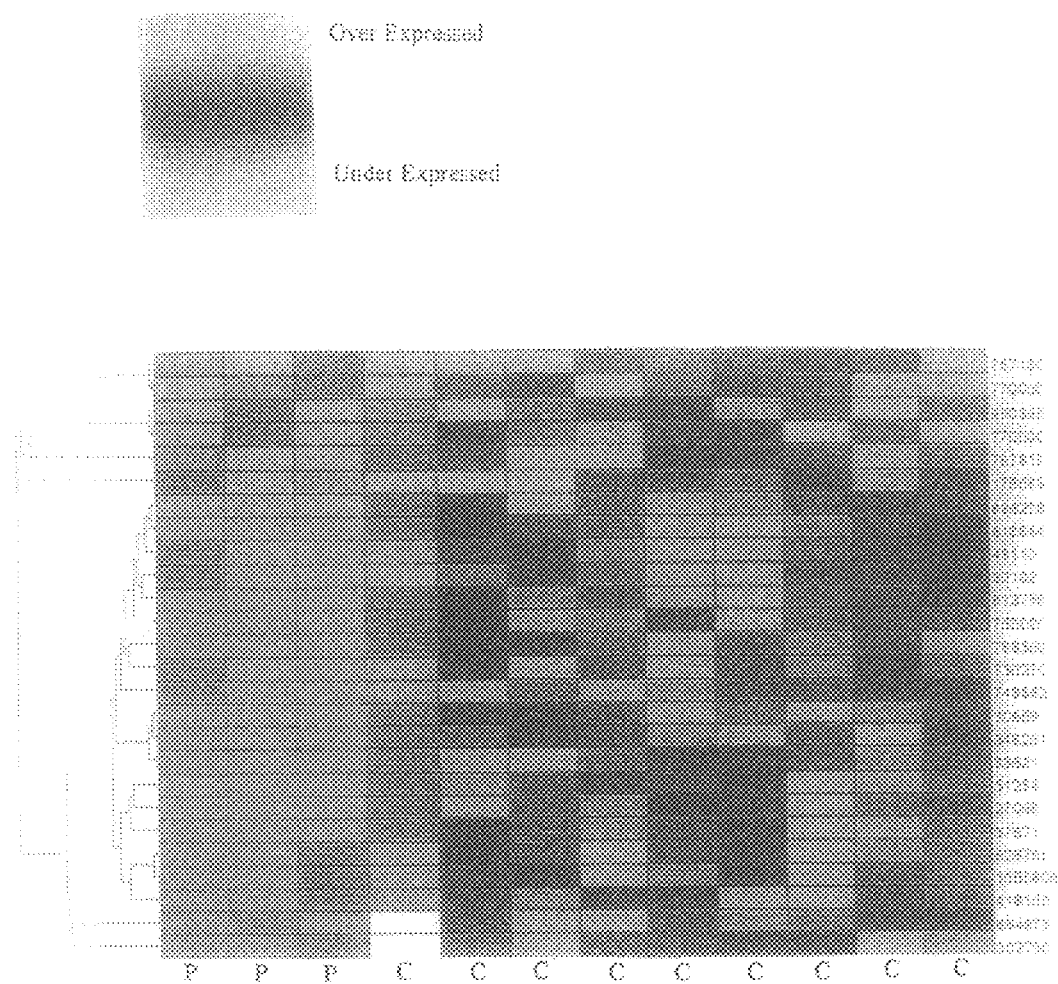
FIG. 7, the showing of the results of microarray determination of gene expression characteristics of FIG. 3, executed in color.
Figure 8:
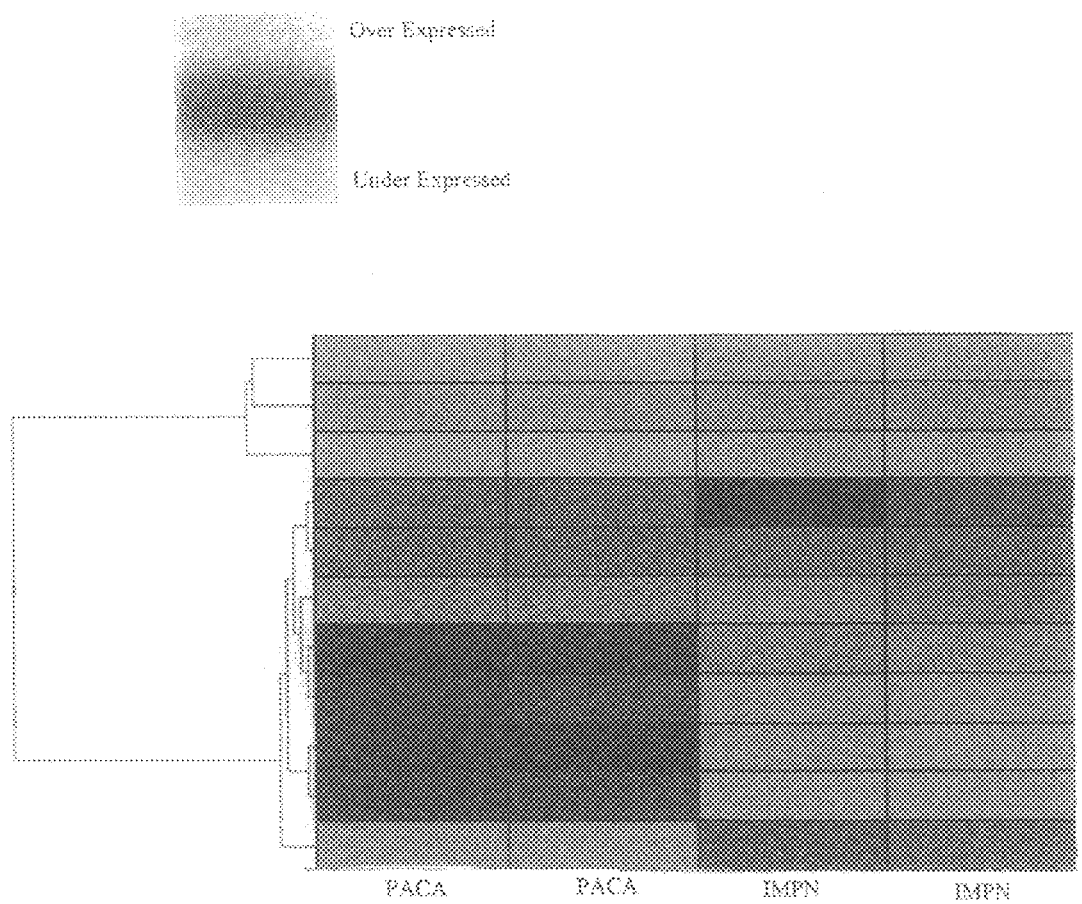
FIG. 8, the showing of the results of microarray determination of gene expression characteristics of FIG. 4, executed in color.

For example, to show that different conditions, even when similar, can be identified, patient differential gene expression patterns were obtained for two patients having known intraductal mucinous pancreatic neoplasm. The patient differential gene expression patterns for these two patients are shown in FIG. 4 in the last two columns labeled IMPN. The gene expression patterns of the two patients known to have ductal pancreatic adenocarcinoma are labeled PA. These two intraductal pancreatic adenocarcinoma patients with intraductal mucinous pancreatic neoplasms were analyzed with a consistent method on human slide B with 9600 genes with Significant Analysis of Microarray (SAM) with the Students T Test and a p value of 0.0001 using Gene Sight software. The consistent patterns of over and under expression of the eleven identified genes allow the establishment of significant patterns characteristic of this intraductal pancreatic cancer state as compared to the other pancreatic conditions. This indicates that the method of the invention can be used to distinguish between different pancreatic conditions, so could be used to distinguish between pancreatic disease conditions including islet cell tumors, other growths, and inflammatory states. This method may be used with breast, lung and colon growths and cancers as well as with donor and recipient organ transplants, both before and after transplantation to identify and allow treatment of possible transplanted organ rejection and other disease conditions related and unrelated to the transplantation.

While the invention has been described with specific reference to pancreatic disease conditions, and expression patterns for specific genes have been identified for use in screening patients for pancreatic disease conditions, the method of the invention can be used for screening various other bodily conditions and in generating patterns for specific genes for use with other bodily conditions, including breast, lung and colon growths and cancers as well as with donor and recipient organ transplants, both before and after transplantation to identify and treat possible transplanted organ rejection and other disease conditions related and unrelated to the transplantation.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

I claim:

1. A method of screening a human patient for the presence of a particular one of the conditions of breast, lung, pancreatic, and colon growths and cancers, comprising the steps of:
    obtaining a gene expression pattern for a set of peripheral blood monocyte-lymphocyte genes predetermined to be likely to differ between people known not to be suffering from a particular one of the conditions for which the patient is being screened and people known to be suffering from the particular one of the conditions for which the patient is being screened;
    obtaining, using RNase free equipment, an undiluted sample of peripheral blood monocyte-lymphocytes from the patient to be screened for the particular one of the conditions for which the patient is being screened, and mixing the undiluted sample with heparin and a ficoll gradient as the sample is taken from the patient;
    separating the monocyte-lymphocytes from the sample of peripheral blood within two hours of obtaining the peripheral blood from the patient;
    processing the separated peripheral blood monocyte-lymphocytes to allow determination of gene expression characteristics of genes from the separated peripheral blood monocyte-lymphocytes;
    determining gene expression characteristics for selected genes from the separated peripheral blood monocyte-lymphocytes, said selected genes including genes the same as genes included in the obtained gene expression pattern for the set of peripheral blood monocyte-lymphocyte genes predetermined to be likely to differ between people known not to be suffering from the particular one of the conditions for which the patient is being screened and people known to be suffering from the particular one of the conditions for which the patient is being screened; and
    comparing the gene expression characteristics determined for the selected genes separated from the peripheral blood monocyte-lymphocytes from the patient which are the same genes as genes included in the set of peripheral blood monocytes-lymphocyte genes predetermined to be likely to differ between people known not to be suffering from the particular one of the conditions for which the patient is being screened and people known to be suffering from the particular one of the conditions for which the patient is being screened with the gene characteristics for the same genes in the set of genes, statistically significant differences between the expression characteristics between at least one of these same genes indicating a likelihood of the existence in the patient of the particular one of the conditions being screened for.

2. A method of screening a human patient for the presence of a particular one of the conditions of breast, lung, pancreatic, and colon growths and cancers, according to claim 1, wherein the obtained gene expression pattern for a set of peripheral blood monocyte-lymphocyte genes predetermined to be likely to differ between people known not to be suffering from the particular one of the conditions for which the patient is being screened and people known to be suffering from the particular one of the conditions for which the patient is being screened is created from a comparison of peripheral blood monocyte-lymphocyte gene expression characteristics from a sample of people known not to be suffering from the condition for which the patient is being screened and peripheral blood monocyte-lymphocyte gene expression characteristics from a sample of people known to be suffering from the condition for which the patient is being screened, and selecting a plurality of the peripheral blood monocyte-lymphocyte genes which show statistically significant different over and under expressions between the peripheral blood monocyte-lymphocyte genes of the two samples of people to make up the predetermined set of genes.

3. A method of screening a human patient for the presence of a particular one of the conditions of breast, lung, pancreatic, and colon growths and cancers, according to claim 2, wherein the peripheral blood monocyte-lymphocytes from which the peripheral blood monocyte-lymphocyte gene expression characteristics from a sample of people known not to be suffering from the condition for which the patient is being screened and peripheral blood monocyte-lymphocyte gene expression characteristics from a sample of people known to be suffering from the condition for which the patient is being screened are obtained from each of the people in each of the samples of people by obtaining a sample of peripheral blood monocyte-lymphocytes from each of the people in each of the samples and mixing each sample with heparin and a ficoll gradient as it is taken, and separating the monocyte-lymphocytes from each sample of peripheral blood within two hours of obtaining the peripheral blood.

4. A method of screening a human patient for the presence of a particular one of the conditions of breast, lung, pancreatic, and colon growths and cancers, according to claim 1, wherein the step of processing the sample of peripheral blood monocyte-lymphocytes to allow determination of gene expression characteristics of genes from the sample peripheral blood monocyte-lymphocytes includes the steps of processing the peripheral blood monocyte-lymphocytes to total RNA, and obtaining amplified aRNA or cDNA from the total RNA.

5. A method of screening a human patient for the presence of a particular one of the conditions of breast, lung, pancreatic, and colon growths and cancers, according to claim 4, wherein the total RNA includes polyadenylated messenger RNA, and the step of obtaining amplified aRNA or cDNA from the total RNA obtains the amplified aRNA or cDNA from the polyadenylated messenger RNA.

6. A method of screening a human patient for the presence of a particular one of the conditions of breast, lung, pancreatic, and colon growths and cancers, according to claim 4, wherein the step of determining gene expression characteristics from the genes from the sample peripheral blood monocyte-lymphocytes obtains a gene expression pattern for the amplified anti-sense aRNA or cDNA.

7. A method of screening a human patient for the presence of a particular one of the conditions of breast, lung, pancreatic, and colon growths and cancers, according to claim 6, wherein the step of determining gene expression characteristics from the genes from the sample peripheral blood monocyte-lymphocytes obtains a gene expression microarray pattern for the amplified anti-sense aRNA or cDNA.

8. A method of screening a human patient for the presence of a particular one of the conditions of breast, lung, pancreatic, and colon growths and cancers, according to claim 1, wherein the step of determining gene expression characteristics from the genes from the sample peripheral blood monocyte-lymphocytes obtains a gene expression microarray pattern for the genes.

9. A method of screening a human patient for the presence of a particular one of the conditions of breast, lung, pancreatic, and colon growths and cancers, according to claim 8, wherein the step of obtaining a sample of peripheral blood monocyte-lymphocytes from the patient includes the step of obtaining a sample of peripheral blood from the patient and the step of separating and obtaining a sample of sets of CD8, CD4, and CD4-CD25 T lymphocytes and B lymphocytes.

10. A method of screening a human patient for the presence of a particular one of the conditions of breast, lung, pancreatic, and colon growths and cancers, according to claim 9, wherein the step of separating and obtaining a sample of sets of CD8, CD4, and CD4-CD25 T lymphocytes and B lymphocytes obtains the sets of CD8, CD4, and CD4-CD25 T lymphocytes and B lymphocytes through negative selection of the cells to total RNA with amplification of polyadenylated messenger RNA to amplified anti-sense aRNA or to cDNA.

11. A method of screening a human patient for the presence of a particular one of the conditions of breast, lung, pancreatic, and colon growths and cancers, according to claim 10, wherein the step of determining gene expression characteristics from the genes from the sample peripheral blood monocyte-lymphocytes obtains a gene expression pattern for the amplified anti-sense aRNA or cDNA.

12. A method of screening a human patient for the presence of a particular one of the conditions of breast, lung, pancreatic, and colon growths and cancers, according to claim 11, wherein the step of determining gene expression characteristics from the genes from the sample peripheral blood monocyte-lymphocytes obtains a gene expression microarray pattern for the amplified anti-sense aRNA or cDNA.

13. A method of screening a human patient for the presence of a particular one of the conditions of breast, lung, pancreatic, and colon growths and cancers, according to claim 1, wherein the step of separating the monocyte-lymphocytes from the sample of peripheral blood within two hours of obtaining the peripheral blood from the patient is the step of separating the monocyte-lymphocytes from the sample of peripheral blood within thirty minutes of obtaining the peripheral blood from the patient.

14. A method of screening a human patient for the presence of a particular one of the conditions of breast, lung, pancreatic, and colon growths and cancers, according to claim 1, wherein the step of processing the separated peripheral blood monocyte-lymphocytes to allow determination of gene expression characteristics of genes from the separated peripheral blood monocyte-lymphocytes is begun immediately after the step of separating the monocyte-lymphocytes from the sample of peripheral blood.

15. A method of screening a human patient for the presence of a particular one of the conditions of breast, lung, pancreatic, and colon growths and cancers, according to claim 1, wherein the separated peripheral blood monocyte-lymphocytes are preserved after separation and wherein the step of processing the separated peripheral blood monocyte-lymphocytes to allow determination of gene expression characteristics of genes from the separated peripheral blood monocyte-lymphocytes is conducted on the preserved monocyte-lymphocytes from the sample of peripheral blood.

16. A method of screening a human patient for the presence of a particular one of the conditions of breast, lung, pancreatic, and colon growths and cancers, according to claim 15, wherein the step of preserving the separated peripheral blood monocyte-lymphocytes includes the step of freezing the separated monocyte-lymphocytes to −80° C. for storage.

17. A method of screening a human patient for the presence of a particular one of the conditions of breast, lung, pancreatic, and colon growths and cancers, according to claim 1, wherein the step of separating the monocyte-lymphocytes from the undiluted sample of peripheral blood includes the steps of centrifuging the sample of undiluted peripheral blood, heparin, and ficoll gradient to obtain a layer of monocytes-lymphocytes, aspirating a portion of the monocyte-lymphocyte layer, washing the monocytes-lymphocytes one time, and centrifuging the monocytes-lymphocytes to concentrate them into a pellet.

* * * * *